(12) United States Patent
Hoshika et al.

(10) Patent No.: US 10,006,392 B2
(45) Date of Patent: Jun. 26, 2018

(54) PHYSICAL QUANTITY DETECTION DEVICE

(71) Applicant: Hitachi Automotive Systems, Ltd., Hitachinaka-shi, Ibaraki (JP)

(72) Inventors: Hiroaki Hoshika, Ibaraki (JP); Takayuki Yogo, Ibaraki (JP); Takahiro Miki, Ibaraki (JP); Takeo Hosokawa, Ibaraki (JP); Yuki Isoya, Ibaraki (JP)

(73) Assignee: Hitachi Automotive Systems, Ltd., Hitachinaka-shi (JP)

( * ) Notice: Subject to any disclaimer, the term of this patent is extended or adjusted under 35 U.S.C. 154(b) by 57 days.

(21) Appl. No.: 15/126,298

(22) PCT Filed: Jan. 7, 2015

(86) PCT No.: PCT/JP2015/050193
§ 371 (c)(1),
(2) Date: Sep. 15, 2016

(87) PCT Pub. No.: WO2015/151535
PCT Pub. Date: Oct. 8, 2015

(65) Prior Publication Data
US 2017/0082051 A1    Mar. 23, 2017

(30) Foreign Application Priority Data
Mar. 31, 2014   (JP) .................................. 2014-073519

(51) Int. Cl.
*F02D 41/18* (2006.01)
*G01D 21/02* (2006.01)
(Continued)

(52) U.S. Cl.
CPC .......... *F02D 41/182* (2013.01); *F02D 37/02* (2013.01); *F02D 41/18* (2013.01); *G01D 3/0365* (2013.01);
(Continued)

(58) Field of Classification Search
None
See application file for complete search history.

(56) References Cited

U.S. PATENT DOCUMENTS 5,632,333 A * 5/1997 Imamura .............. B01D 53/265
                                                        165/228
6,182,644 B1    2/2001 Kotwicki et al.
(Continued)

FOREIGN PATENT DOCUMENTS

JP      3-78650 A     4/1991
JP      9-113310 A    5/1997
(Continued)

OTHER PUBLICATIONS

Extended European Search Report issued in counterpart European Patent Application No. 15773168.8 dated Oct. 6, 2017 (Eight (8) pages).
(Continued)

*Primary Examiner* — Paul West
*Assistant Examiner* — Mark A Shabman
(74) *Attorney, Agent, or Firm* — Crowell & Moring LLP (57) ABSTRACT

To achieve a physical quantity detection device capable of obtaining a desired overall device accuracy without unnecessarily raising the tolerances of detection elements, the present invention is characterized by having a plurality of physical quantity detection units for respectively detecting plurality of physical quantities, a storage unit for storing the error characteristics of individual physical quantity detection units, a physical quantity calculation unit for using at least two physical quantities detected by at least two of the plurality of physical quantity detection units to calculate a separate physical quantity, and an error calculation unit for reading the error characteristics of the plurality of physical (Continued)

quantity detection units from the storage unit and calculating the error of the separate physical quantity.

4 Claims, 8 Drawing Sheets

(51) Int. Cl.
G01D 3/036 (2006.01)
F02D 37/02 (2006.01)
G01N 27/22 (2006.01)
G01N 33/00 (2006.01)
G01N 27/12 (2006.01)
F02D 41/28 (2006.01)

(52) U.S. Cl.
CPC ........... *G01D 21/02* (2013.01); *G01N 27/223* (2013.01); *G01N 27/228* (2013.01); *G01N 33/0073* (2013.01); *F02D 2041/281* (2013.01); *F02D 2041/286* (2013.01); *F02D 2200/0414* (2013.01); *F02D 2200/0418* (2013.01); *G01N 27/121* (2013.01)

(56) References Cited

U.S. PATENT DOCUMENTS

| 2004/0012912 | A1 | 1/2004 | Rombach |
| 2008/0072669 | A1* | 3/2008 | Paukkunen ............. G01W 1/08 73/335.02 |
| 2011/0107832 | A1 | 5/2011 | Sakuma |
| 2013/0024091 | A1 | 1/2013 | Yun et al. |
| 2014/0121948 | A1* | 5/2014 | Marlett ..................... F01N 9/00 701/104 |

FOREIGN PATENT DOCUMENTS

| JP | 10-2772 A | 1/1998 |
| JP | 2004-503746 A | 2/2004 |
| JP | 2011-99757 A | 5/2011 |
| JP | 2014-48246 A | 3/2014 |

OTHER PUBLICATIONS

International Search Report (PCT/ISA/210) issued in PCT Application No. PCT/JP2015/050193 dated Apr. 14, 2015 with English translation (5 pages).
Japanese-language Written Opinion (PCT/ISA/237) issued in PCT Application No. PCT/JP2015/050193 dated Apr. 14, 2015 (3 pages).

* cited by examiner

PHYSICAL QUANTITY DETECTION DEVICE

TECHNICAL FIELD

The present invention relates to physical quantity detection device for detecting a physical quantity such as a temperature and a humidity of intake air taken by an internal combustion engine of an automobile.

BACKGROUND ART

In PTL 1, a structure of a humidity detection device is disclosed. The humidity detection device includes a humidity sensing element, a temperature sensing element, and a ROM which has previously stored output characteristics and a temperature coefficient of the humidity sensing element arranged in a sensor probe, calculates a detection temperature by using a temperature detecting value of the temperature sensing element and referring to a storage table for managing the temperature in the ROM, and calculates a detection humidity by using the detection temperature and a humidity detecting value of the humidity sensing element and referring to a characteristics data storage table in the ROM.

PTL 2 discloses a technique of a sensor device which includes an EPROM in which data to correct characteristics variation of the sensor and machine differences has been previously stored and transmits a signal in which the corrected data is added to collected physical information corresponding data to a sensor signal processing device.

CITATION LIST

Patent Literature

PTL 1: JP 3-78650 A
PTL 2: JP 9-113310 A

SUMMARY OF INVENTION

Technical Problem

As the humidity detection device in PTL 1, an indirect physical quantity calculated by using detection values of a plurality of detection elements includes an error included in the detection value of the detection element. For example, even when the detection elements have the same tolerances, the single detection element has characteristics different from the other detection element. Therefore, the physical quantity to be calculated is different according to a combination of the detection elements. When a tolerance of each detection element is raised and an allowable error is reduced as possible to obtain a desired accuracy of the physical quantity to be calculated, a percent defective of the detection element and the cost are increased.

Also, as the sensor device in PTL 2, when the physical quantity is corrected by outputting the correction data of the detection element to the sensor signal processing device, it is necessary to consider the characteristics of each sensor. It is necessary to perform a complicated error calculation by the sensor signal processing device.

The present invention has been made to solve the above problems. A purpose of the present invention is to obtain a physical quantity detection device which can obtain a desired overall device accuracy without unnecessarily raising tolerances of detection elements.

Solution to Problem

In order to solve the above problems, for example, a structure described in CLAIMS is employed. The present invention includes a plurality of solutions to solve the above problem. As an example, the present invention includes a plurality of physical quantity detection units which detects a plurality of physical quantities, a storage unit for storing error characteristics of the respective physical quantity detection units, a physical quantity calculation unit for calculating another physical quantity by using at least two physical quantities detected by at least two physical quantity detection units of the plurality of physical quantity detection units, and an error calculation unit for calculating an error of the another physical quantity by reading the error characteristics of the physical quantity detection units from the storage unit.

Advantageous Effects of Invention

According to the present invention, a desired overall device accuracy can be obtained without unnecessarily increasing detection accuracy of each detection unit. A problem, a structure, and an effect other than those described above are described in the embodiment below.

DESCRIPTION OF EMBODIMENTS

Next, one embodiment of a physical quantity detection device according to the present invention is described below with reference to the drawings.

Figure 1:
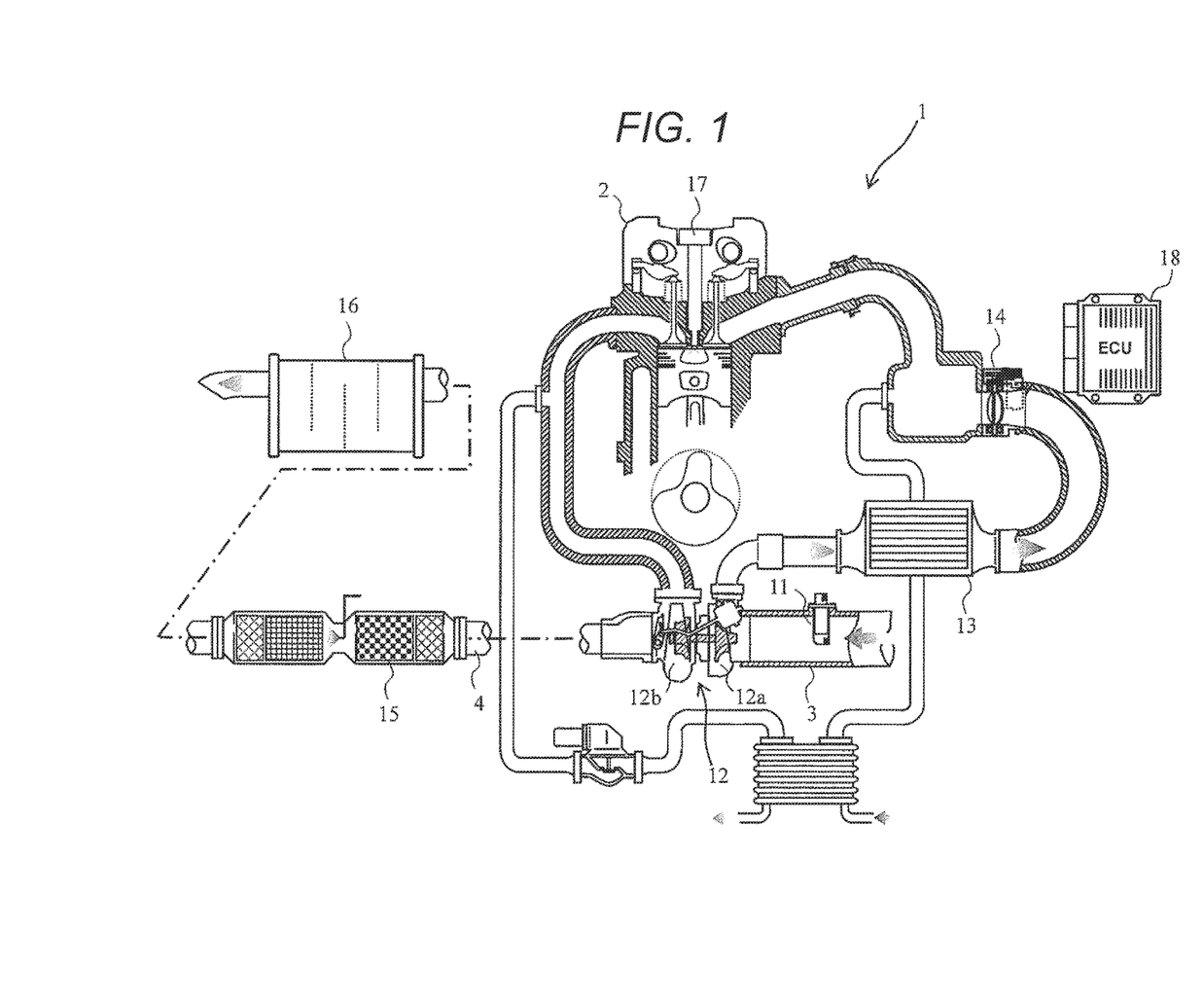
FIG. 1 is a schematic diagram of an engine control system to which a physical quantity detection device according to the present invention is applied.
Figure 2:
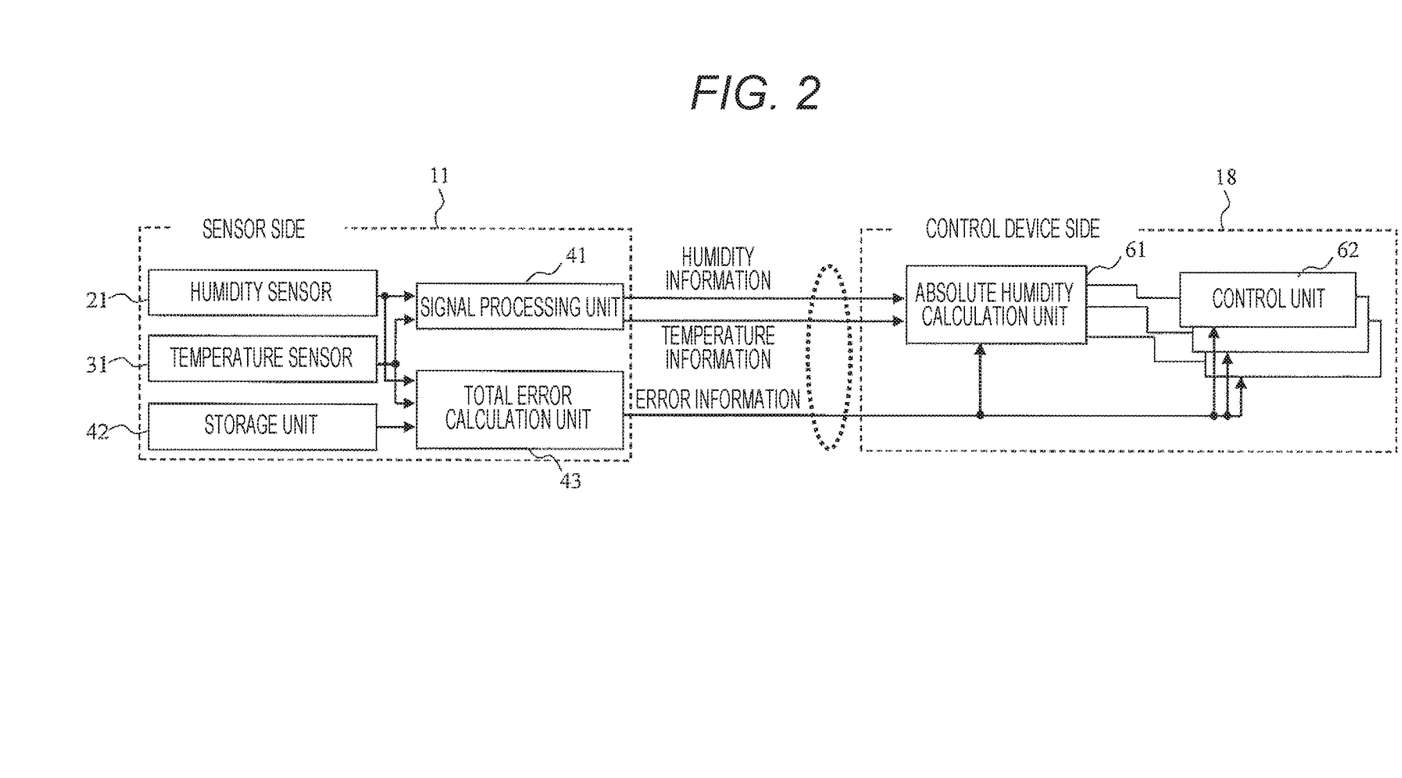
FIG. 2 is a function block diagram to describe an embodiment of the physical quantity detection device according to the present invention.

FIG. 1 is a schematic diagram of an engine control system to which the physical quantity detection device according to the present invention is applied, and FIG. 2 is a function block diagram to describe an embodiment of the physical quantity detection device according to the present invention.

The physical quantity detection device is built into an engine control system 1 of an automobile. As illustrated in FIG. 1, the engine control system 1 includes an engine body 2 which is an internal combustion engine, an air intake passage 3 to supply intake air to the engine body 2, and an exhaust passage 4 to exhaust exhaust gas from the engine body 2. At the middle position of the air intake passage 3, a compressor 12a of a turbocharger 12 is interposed, and an air flow sensor 11 is arranged at a position on the upstream side of the compressor 12a. An intercooler 13, an electric control throttle valve 14, a supercharging pressure sensor, and the like are arranged on the downstream side of the compressor 12a.

A turbine 12b of the turbocharger 12 is provided at the middle position of the exhaust passage 4, and a catalyst 15 and a muffler 16 are arranged on the downstream side of the turbine 12b. A high pressure fuel injector 17 for injecting fuel in a combustion chamber and an ignition plug which is not shown are attached to the engine body 2. Also, a crank angle sensor for detecting an engine speed, a water temperature sensor for detecting a cooling water temperature of the engine body, and the like are attached.

The air flow sensor 11 includes a flow rate sensor to detect a flow rate which is one of physical quantities of the intake air. In addition, the air flow sensor 11 includes a humidity sensor 21 to detect a relative humidity of the intake air and a temperature sensor 31 (refer to FIG. 2) to detect the temperature of the intake air. That is, in the present embodiment, the humidity sensor 21 and the temperature sensor 31 are provided in the air flow sensor 11.

Each sensor signal of the flow rate sensor, the humidity sensor 21, the temperature sensor 31, the crank angle sensor, the water temperature sensor, and the like of the air flow sensor 11 is input to an ECU 18 which is a control device of the engine control system 1. Each sensor signal is used for various engine operation control such as ignition timing control and fuel injection control.

Figure 3A:
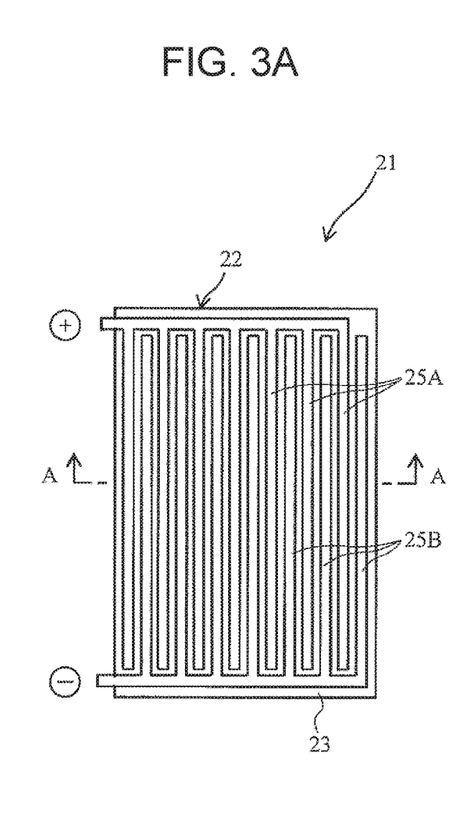
FIGS. 3A and 3B are diagrams of an exemplary structure of a humidity sensor.
Figure 3B:
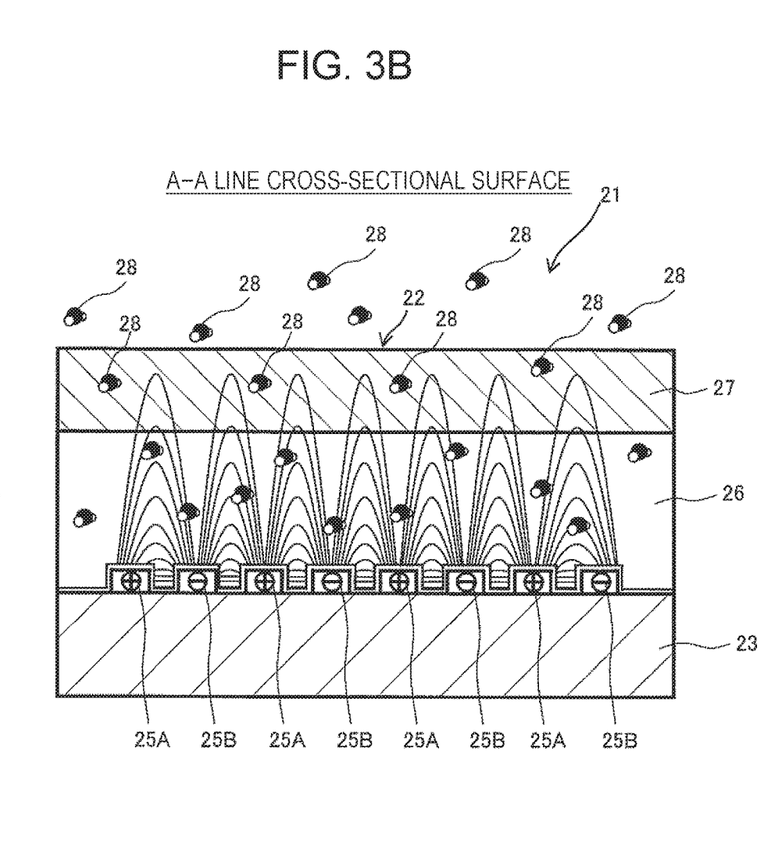
Figure 4:
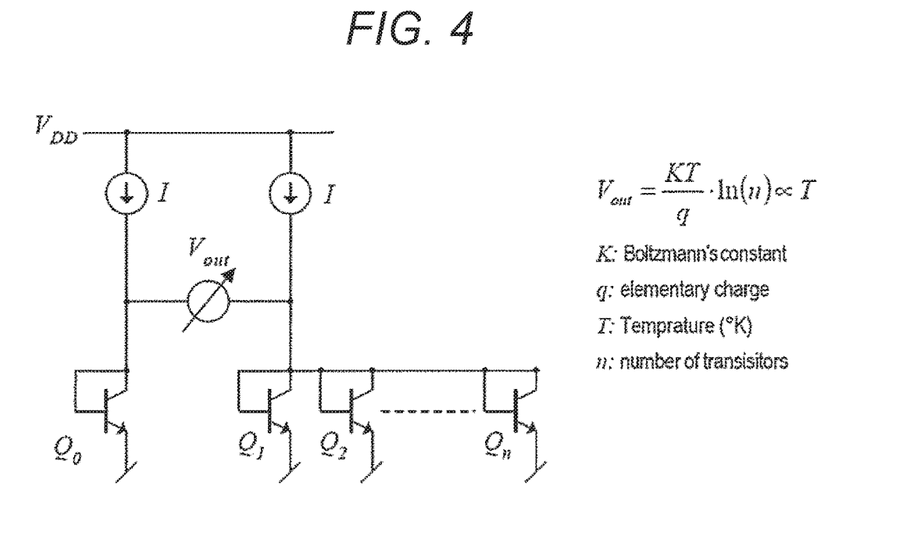
FIG. 4 is a diagram of an exemplary structure of a temperature sensor.

FIGS. 3(a) and 3(b) are diagrams of an exemplary structure of the humidity sensor. FIG. 3(a) is a front view of the humidity sensor, and FIG. 3(b) is a cross-sectional diagram taken along a line A-A of FIG. 3(a). FIG. 4 is a diagram of an exemplary structure of the temperature sensor. A known humidity sensor 21 and a known temperature sensor 31 can be used.

The humidity sensor 21 is an electrostatic capacitance type relative humidity sensor and includes a sensor element 22 for detecting the humidity. As illustrated in FIGS. 3(a) and 3(b), the sensor element 22 has structure in which a comb-shaped electrode pair 25A and 253 is provided on the upper surface of a silicon substrate 23 and the comb-shaped electrode pair 25A and 25B is covered with a hygroscopic high-molecular polymer film 26. The capacitance of the electrode pair 25A and 25B changes due to moisture absorption of the high-molecular polymer film 26. The capacitance change has a high correlation with the relative humidity. When the capacitance is measured, the relative humidity can be detected. There are several types of electrode structures. In some of them, polymer is sandwiched between the upper and lower electrodes. A protection film 27 is provided on the upper surface of the high-molecular polymer film 26, and the intake air passes through the outside of the protection film 27. Then, water molecules 28 are absorbed by the high-molecular polymer film 26.

The temperature sensor 31 is provided near the humid it sensor 21 to measure the temperature near the humidity sensor 21. For example, as an exemplary circuit structure is illustrated in FIG. 4, a band gap type semiconductor temperature sensor can be used as the temperature sensor 31.

As illustrated in FIG. 2, the air flow sensor 11 includes a signal processing unit 41, a storage unit 42, and a total error calculation unit 43 in addition to the humidity sensor 21 and the temperature sensor 31.

The signal processing unit 41 performs processing for generating humidity information which is information on the relative humidity of the intake air and temperature information which is information on the temperature of the intake air by processing signals of the humidity sensor 21 and the temperature sensor 31 and outputting them to the ECU 18.

Figure 6A:
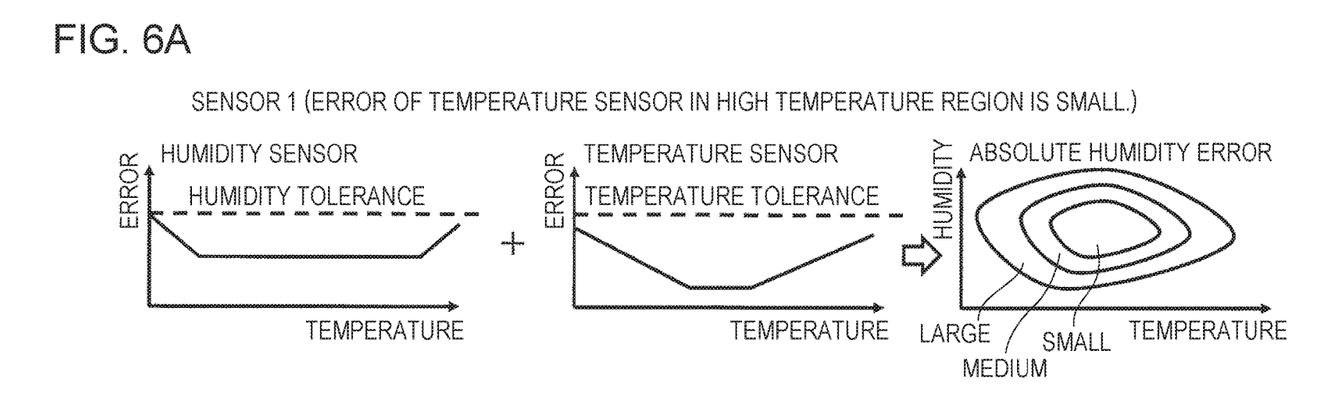
FIGS. 6A and 6B are diagrams to describe a relation of an absolute humidity error obtained from temperature characteristics of the humidity sensor and temperature characteristics of the temperature sensor.
Figure 6B:
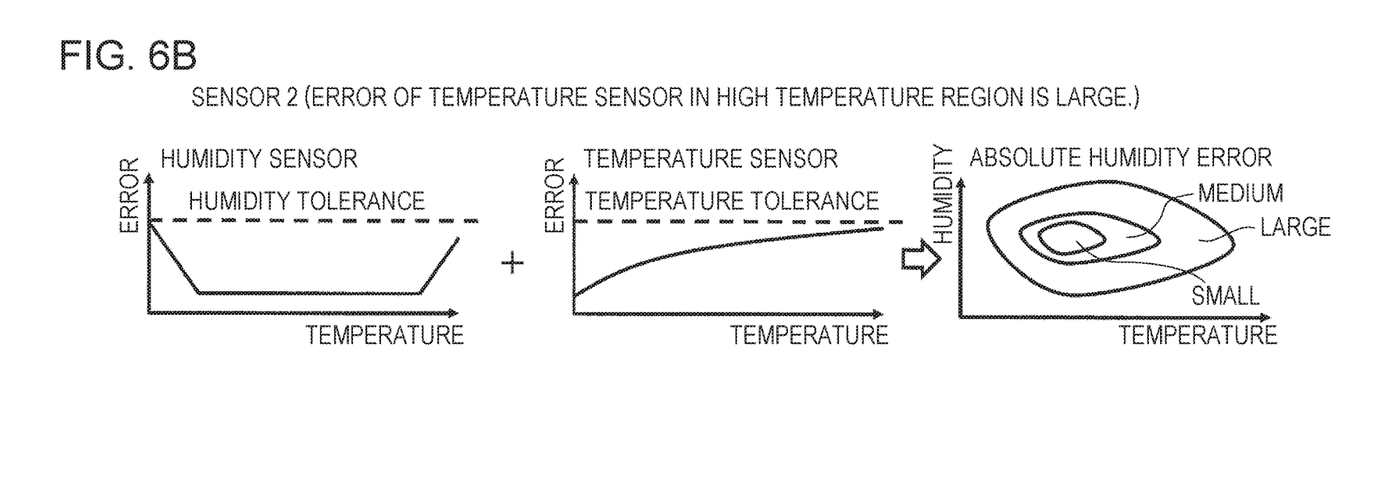

The storage unit 42 stores error characteristics indicating a change of an error according to the temperature (refer to FIG. 6) as specific information on the humidity sensor 21 and the temperature sensor 31. The error characteristics of the respective sensors are different from each other, and the sensor having the error characteristics within a range of a pre-set tolerance is used.

The total error calculation unit 43 calculates an error of the absolute humidity which is the total error by using the error characteristics of the relative humidity sensor 21 and the error characteristics of the temperature sensor 31 stored in the storage unit 42 and outputs the calculation result to the ECU 18. The total error calculation unit 43 calculates the total error at the time of calculating the absolute humidity which is an indirect physical quantity by using a combination of the errors without using the respective errors of the humidity sensor 21 and the temperature sensor 31.

The total error calculation unit 43 calculates the total error by conducting a search by using the temperature information and the humidity information which are the two physical quantities or by conducting a search according to the axis corresponding to each physical quantity from a map arranged in a grid shape or a plurality of tables.

The air flow sensor 11 is connected to the ECU 18 with a communication cable, and communication using digital signals is performed by using communication standards such as the SENT, the LIN, and the CAN. The sensor information output from the air flow sensor 11 to the ECU 18 is superimposed by digital communication by using a single or double communication cables and is output. The error information stored in the storage unit 42 is collectively output to the ECU 18 according to a request from outside or a time from power supply or the number of times to output the signals by the sensor.

An absolute humidity calculation unit 61 of the ECU 18 calculates the absolute humidity based on the humidity information and the temperature information output from the air flow sensor 11 and corrects the absolute humidity based on the total error calculated by the total error calculation unit 43. The corrected absolute humidity calculated by the absolute humidity calculation unit 61 is used for various engine operation control by a control unit 62 of the ECU 18. Also, the ECU 18 can directly use the information on the total error for various engine operation control.

Figure 5:
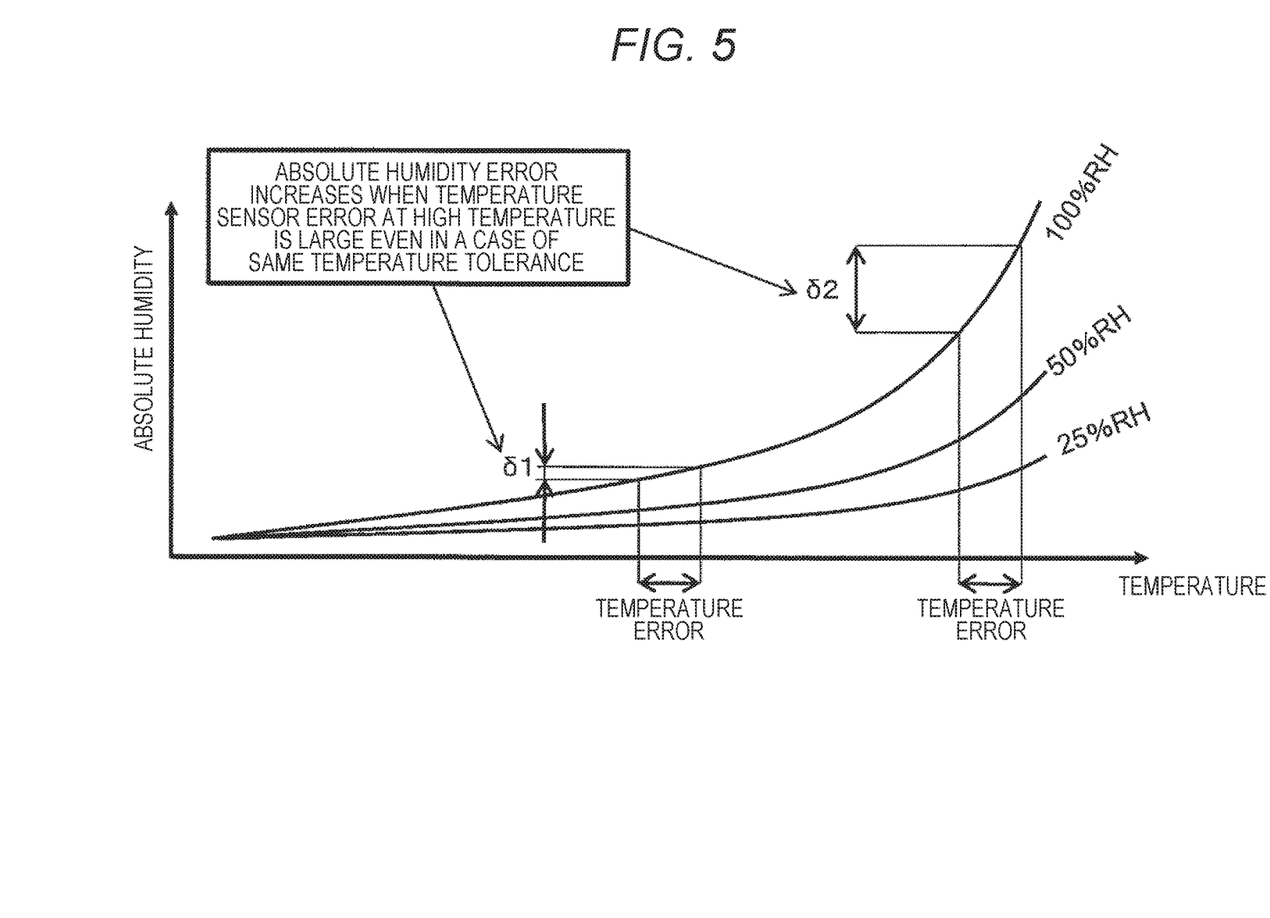
FIG. 5 is an air diagram of a relation between a temperature of intake air, an absolute humidity, and a relative humidity.

FIG. 5 is an air diagram of a relation between a dry-bulb temperature, the absolute humidity, and the relative humidity of the intake air. FIGS. 6(a) and 6(b) are diagrams to describe the total error of the absolute humidity obtained from the error characteristics of the humidity sensor and the temperature sensor.

As described above, in the present embodiment, the absolute humidity is obtained from the two physical quantities, i.e., the temperature and the relative humidity. When the absolute humidity is calculated by using the temperature and the relative humidity, as illustrated in the air diagram in FIG. 5, the temperature has more effect than that of the humidity, and the absolute humidity to be obtained is largely different especially in the high temperature region even when the temperatures are slightly different. For example, when the temperature tolerances are the same, an absolute humidity error $\delta 2$ at the time when a temperature error is generated on a high temperature side is larger than an absolute humidity error $\delta 1$ at the time when a temperature error is generated on a low temperature side ($\delta 1 << \delta 2$).

Therefore, even when the humidity sensor 21 and the temperature sensor 31 have the same tolerances, the absolute humidity to be obtained is different according to the error characteristics of each sensor. For example, when a sensor 1 illustrated in FIG. 6(a) is compared with a sensor 2 illustrated in FIG. 6(b), an error of the temperature sensor of the sensor 2 from the middle temperature region to the high temperature region is larger than that of the temperature sensor of the sensor 1. Therefore, when the total error of the absolute humidity of the sensor 1 is compared with that of the sensor 2, the error in the high temperature region of the sensor 2 is larger than that of the sensor 1. Accordingly, the temperature sensor of the sensor 1 and the temperature sensor of the sensor 2 have the same tolerances, the total errors of the absolute humidities and the absolute humidities to be obtained are different from each other.

Figure 8:
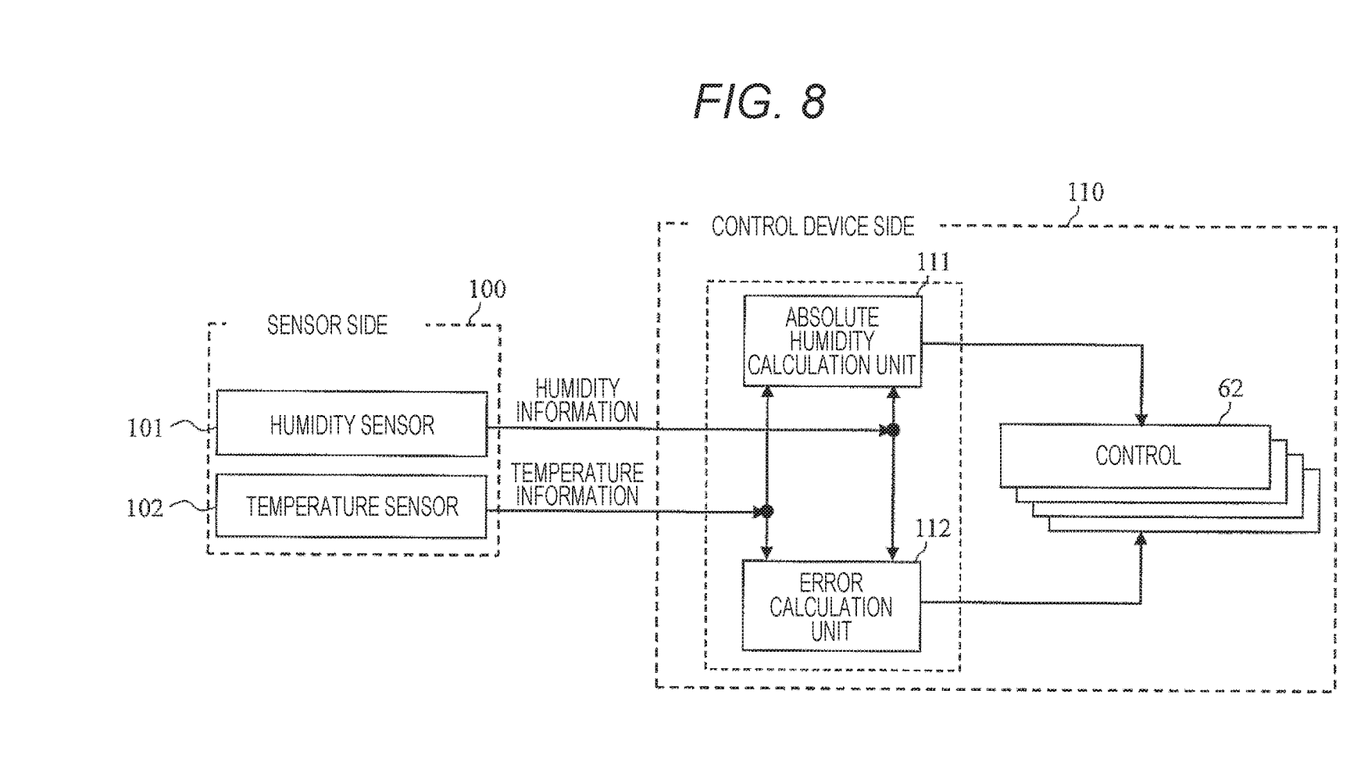
FIG. 8 is a diagram to describe a problem of the related art.

FIG. 8 is a diagram to describe the related art and a function block diagram of a traditional physical quantity detection device.

Generally, a traditional sensor 100 has measured physical quantities such as the humidity and the temperature by using a humidity sensor 101 and a temperature sensor 102 and has output them by modulating them to indirect physical phenomenon such as a voltage and a signal frequency. The above information is taken and processed by an ECU 110 and is combined with information on other sensor and the like by the absolute humidity calculation unit 111 and the error calculation unit 112 of the ECU 110. Then, the information is used to perform correction to other physical quantity and the like and perform control. For example, the absolute humidity calculation unit 111 obtains the absolute humidity from the humidity information of the humidity sensor 101 and the temperature information of the temperature sensor 102. Since both the humidity sensor 101 and the temperature sensor 102 have the tolerances and temperature characteristics, the total error is complicated. The error of the absolute humidity gets worse according to the temperature so that the information of the absolute humidity cannot be used. Therefore, in order to obtain and use the absolute humidity by the error calculation unit 112 of the ECU 110, it is necessary to perform complicated error management. However, calculation processing to calculate the error is very complicated, and a development cost is needed.

Whereas, as illustrated in FIG. 2, the physical quantity detection device according to the present invention has the storage unit 42 and the total error calculation unit 43 in the air flow sensor 11 on the sensor side. The total error calculation unit 43 calculates the total error at the time of calculating the absolute humidity which is the indirect physical quantity by combining the respective errors of the humidity sensor 21 and the temperature sensor 31 by using the error characteristics of the humidity sensor 21 and the temperature sensor 31 stored in the storage unit 42 and outputs it to the ECU 18.

In the present invention, the storage unit 42 stores the tolerance generated at the time of calculating the absolute humidity, and the absolute humidity error obtained from each error characteristics is transmitted separately from the sensor signal. Therefore, even when the tolerances of the humidity sensor 21 and the temperature sensor 31 are not unnecessarily raised, a desired overall device accuracy of the absolute humidity can be obtained.

Figure 7:
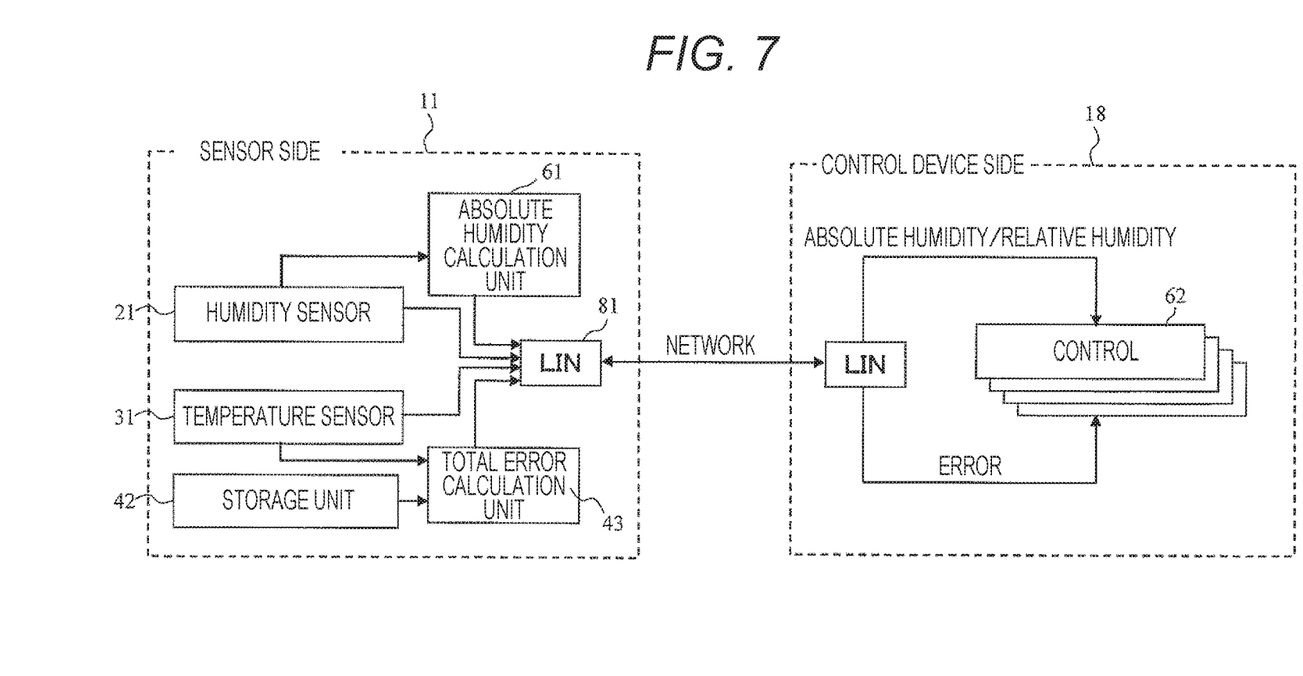
FIG. 7 is a function block diagram to describe another embodiment of a physical quantity detection device according to the present invention.

FIG. 7 is a function block diagram to describe another embodiment of a physical quantity detection device according to the present invention. The characteristics of the present embodiment are to provide an absolute humidity calculation unit 61 in an air flow sensor 11. The place where the absolute humidity calculation unit 61 is provided is not limited to an ECU 18, and the absolute humidity calculation unit 61 may be provided in the air flow sensor 11.

The embodiments of the present invention have been described in detail above. However, the present invention is not limited to the embodiments, and designs can be variously changed without departing from the spirit of the present invention described in CLAIMS. For example, the embodiments have been described in detail for easy understanding of the present invention. The embodiments are not limited to those including all the components described above. Also, a part of the components of the embodiment can be replaced with that of the other embodiment, and the components of the embodiment can be added to the other embodiment. In addition, a part of the components of each embodiment can be deleted, replaced with that of the other embodiment, and a part of the other embodiment can be added to the components of the embodiment.

REFERENCE SIGNS LIST 1 engine control system
11 air flow sensor
21 humidity sensor (first physical quantity detection unit)
31 temperature sensor (second physical quantity detection unit)
41 signal outputting unit
42 storage unit
43 total error calculation unit
61 absolute humidity calculation unit (third physical quantity calculation unit)

The invention claimed is:

1. A physical quantity detection device comprising:
a plurality of physical quantity detection units including a relative humidity sensor and a temperature sensor configured to detect a plurality of physical quantities, the plurality of physical quantities including at least a relative humidity of an intake air of an internal combustion engine detected by the relative humidity sensor and the temperature of the intake air of the internal combustion engine detected by a temperature sensor;
a storage unit configured to store error characteristics of the respective physical quantity detection units, the error characteristics indicating a change of an error according to the temperature;
a physical quantity calculation unit configured to calculate an absolute humidity by using the detected relative humidity and the detected temperature; and
a total error calculation unit configured to calculate a total error of the absolute humidity by reading and using the error characteristics of the relative humidity sensor and the temperature sensor stored in the storage unit.

2. The physical quantity detection device according to claim 1, wherein
information on the total errors of the first and second physical quantities is joined.

3. The physical quantity detection device according to claim 2, wherein
the total error calculation unit calculates the total error of the third physical quantity by conducting a search in a map arranged in a grid shape or a plurality of tables by using the first and second physical quantities.

4. The physical quantity detection device according to claim 3, wherein
the total error calculation unit collectively outputs the information on the total error according to a request from outside or a time from power supply.

* * * * *